United States Patent [19]
Jackson

[11] Patent Number: 6,020,504
[45] Date of Patent: Feb. 1, 2000

[54] PROCESS FOR THE PREPARATION OF CHROMAN DERIVATIVES

[75] Inventor: Barry Jackson, Brig-Glis, Switzerland

[73] Assignee: Lonza AG, Gampel/Valais, Switzerland

[21] Appl. No.: 09/188,355

[22] Filed: Nov. 10, 1998

[30] Foreign Application Priority Data

Nov. 11, 1997 [CH] Switzerland ............ 2601/97

[51] Int. Cl.[7] .............. C07D 311/58; C07D 311/70; C07D 311/72
[52] U.S. Cl. .......................... 549/407
[58] Field of Search ............................ 549/407

[56] References Cited

U.S. PATENT DOCUMENTS

| | | | |
|---|---|---|---|
| 4,344,886 | 8/1982 | Horner et al. | 549/408 |
| 5,364,946 | 11/1994 | Laffan | 549/407 |

FOREIGN PATENT DOCUMENTS 1925112  1/1970  Germany.

OTHER PUBLICATIONS

Bolon, J. Org. Chem., 35(11), 1970, 3666–3670.
Wan et al., Can. J. Chem., 74, 1996, 465–475.
T. Yoshioka et al., J. Med. Chem., (1989), 32, pp. 421–428.
*Comprehensive Heterocyclic Chemistry*, (Ed.: A. J. Boulton and A. McKillop), Pergamon Press, Oxford, vol. 3 Part 2B, pp. 778–787.
*L. I. Smith and R. B. Carlin*, J. Am. Chem Soc., (1942), 64, pp. 524–527.

*Primary Examiner*—Fiona T. Powers
*Attorney, Agent, or Firm*—Fisher, Christen & Sabol

[57] ABSTRACT

Chroman derivatives of the general formula:

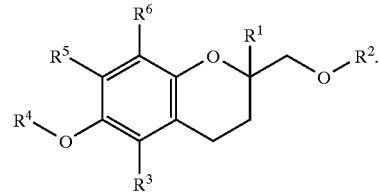

I in which $R^1$ is hydrogen or $C_{1-4}$-alkyl; $R^2$ is $C_{1-6}$-alkyl, $C_{3-6}$-cycloalkyl, optionally substituted aryl or optionally substituted aryl-$C_{1-6}$-alkyl; $R^3$, $R^5$ and $R^6$ independently of one another are hydrogen, halogen, $C_{1-4}$-alkyl or optionally substituted aryl; and $R^4$ is $C_{1-6}$-alkyl, $C_{3-6}$-cycloalkyl, ($C_{1-6}$-alkoxy)methyl, optionally substituted aryl, optionally substituted aryl-$C_{1-6}$-alkyl, C-alkanoyl or optionally substituted aroyl, are obtained from hydroquinone derivatives and alkenes in the presence of Lewis acids. The chroman derivatives (I) are intermediates in the synthesis of pharmaceutical active ingredients, for example, of hypolipidemics.

16 Claims, No Drawings

PROCESS FOR THE PREPARATION OF CHROMAN DERIVATIVES

BACKGROUND OF THE INVENTION

1. Field Of The Invention

The invention relates to a process for the preparation of chroman derivatives of the general formula:

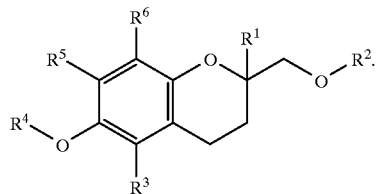

I in the formula, in which:

$R^1$ is hydrogen or $C_{1-4}$-alkyl, $R^2$ is $C_{1-6}$-alkyl, $C_{3-6}$-cycloalkyl, optionally substituted aryl or optionally substituted aryl-$C_{1-6}$-alkyl, $R^3$, $R^5$ and $R^6$ independently of one another are hydrogen, halogen, $C_{1-4}$-alkyl or optionally substituted aryl, and $R^4$ is $C_{1-6}$-alkyl, $C_{3-6}$-cycloalkyl, (C-$_{1-6}$-alkoxy)methyl, optionally substituted aryl, optionally substituted aryl-$C_{1-6}$-alkyl, $C_{1-6}$-alkanoyl or optionally substituted aroyl.

Compounds of this type are intermediates for the synthesis of pharmaceutical active ingredients, e.g., of hypolipidemics [T. Yoshioka et al., *J. Med. Chem.,* (1989), 32, 421–428].

2. Background Art

Known syntheses of the chroman derivatives (I) start from correspondingly substituted hydroquinones, for example, 3-(2,5-dihydroxyphenyl)propan-1-ols [see, e.g.: *Comprehensive Heterocyclic Chemistry,* (Ed.: A. J. Boulton and A. McKillop), Pergamon Press, Oxford, Vol. 3, Part 2B, pp. 778 et seq.]. These starting materials are cyclodehydrated to give chroman-2-carboxylic esters, whose ester function is reduced and whose resulting hydroxymethyl group is etherified to give the title chroman derivative compound (I). The process is, however, relatively involved.

BROAD DESCRIPTION OF THE INVENTION

The object of the invention is to provide an alternative preparation process which produces the desired compounds (I) in a few stages. This object is achieved by the process according to the invention.

It has been found that hydroquinone derivatives of the general formula:

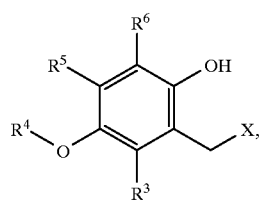

II in which $R^3$ to $R^6$ are as defined above, and X is a leaving group, can be reacted with alkenes of the general formula:

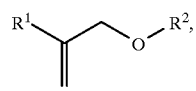

III in which $R^1$ and $R^2$ are as defined above, in the presence of a Lewis acid to give the chroman derivative compounds (I) in only one stage.

DETAILED DESCRIPTION OF THE INVENTION

The process according to the invention presumably proceeds via an o-quinone methide [P. Wan et al., *Can. J. Chem.,* (1996), 74, 465–475] as intermediate.

The hydroquinone derivatives (II) are known compounds or can be prepared in an analogous manner to known compounds.

Examples of suitable leaving groups (X) are halogen, in particular chlorine or bromine, hydroxyl, or ester functions such as alkanoate or sulfonate, for example, acetate or tosylate. Possible synthesis routes are, for example, the halomethylation of the corresponding hydroquinones, the side-chain-halogenation of the corresponding methyl compounds, or the exchange of the hydroxyl group in the corresponding methyl compounds, or the exchange of the hydroxyl group in the corresponding hydroxymethyl compounds for halogen, alkanoate or sulfonate. The hydroxymethyl compounds can, for example, be prepared by hydroxymethylation of the corresponding hydroquinones or by reduction of the corresponding aldehydes or carboxylic acid derivatives. The alkenes (III) are also known compounds or can be prepared in an analogous manner to with known compounds. Since these contain an ether function, suitable methods for their preparation are customary ones for the preparation of unsymmetrical ethers, for example, the Williamson synthesis and related reactions.

Herein, $C_{1-n}$-alkyl is in each case taken to mean all primary, secondary and tertiary linear or branched alkyl groups having from 1 to n carbon atoms, thus, for example, $C_{1-6}$-alkyl is taken to mean methyl, ethyl, propyl, butyl, pentyl, hexyl, isopropyl, isobutyl, isopentyl, isohexyl, sec-butyl, tert-butyl, neopentyl, etc. Correspondingly, $C_{1-6}$-alkoxy and $C_{1-6}$-alkanoyl are taken to mean the groups consisting of hydrogen or $C_{1-6}$-alkyl and carbonyl, respectively.

$C_{3-6}$-Cycloalkyl is taken to mean cyclopropyl, cyclobutyl and, in particular, cyclopentyl and cyclohexyl.

Aryl is taken to mean mono- and polycyclic carbo- and heterocyclic aromatic radicals, for example, phenyl, naphthyl, pyridyl, furyl, thiophenyl, pyrrolyl or indolyl. Correspondingly, aroyl is taken to mean the groups consisting of aryl and carbonyl.

The aryl or aroyl groups can optionally carry one or more identical or different substituents, in particular, groups such as halogen, $C_{1-4}$-alkyl, $C_{1-4}$-perfluoroalkyl, $C_{1-4}$-alkoxy, nitro or $C_{1-4}$-alkanoyl. In principle, all substituents stable under the reaction conditions are possible.

The process according to the invention is preferably used to prepare those chroman derivatives (I) in which $R^1$ is a methyl group. The methallyl ethers (III, $R^1$=Me) required as the starting material in this case can be prepared, for example, from the commercially available methallyl chloride.

Preference is also given to preparing those chroman derivatives in which $R^2$ is an optionally substituted aryl group.

The aryl ethers (III, $R^2$=aryl) which are used as the starting material in this case can be prepared, for example, from the corresponding alkali metal phenoxides and a corresponding alkenyl halide.

Particular preference is given to the preparation of chroman derivatives (I) in which $R^2$ is p-nitrophenyl or p-formylphenyl.

Preference is also given to the preparation of chroman derivatives (I) in which $R^3$, $R^4$, $R^5$ and $R^6$ are methyl groups. The hydroquinone derivative (II, $R^3$=$R^5$=$R^6$=Me) required here as the starting material can be synthesized from commercially available trimethylhydroquinone.

Similarly, the preparation of those chroman derivatives (I) in which $R^4$ is an acetyl group is preferred.

The hydroquinone derivative (II) is preferably one in which X is chlorine, i.e., a chloromethyl compound.

The Lewis acid can, in principle, be any of the Lewis acids customarily used as catalyst in organic synthesis, preferably those from the group incorporating boron trifluoride, aluminium chloride, titanium(IV) chloride, scandium trifluoromethanesulfonate, iron(III) chloride, zirconium(IV) chloride and tin(IV) chloride.

Suitable solvents are, in particular, aprotic solvents of low to average polarity, for example, halogenated hydrocarbons, ethers or esters. Preference is given to dichloromethane, chloroform, tetrahydrofuran and ethyl acetate and mixtures thereof.

The reaction is advantageously carried out at a temperature of from 0° to 100° C., preferably from 20° to 80° C.

The examples below illustrate how the process according to the invention is carried out without any limitation thereof being intended therein.

EXAMPLE 1

6-Acetoxy-2,5,7,8-tetramethyl-2-[(nitrophenoxy)methyl]chroman $(I, R^1=R^3=R^5=R^6=Me, R^2=4-C_6H_4NO_2, R^4=Ac)$ 2.43 g (10 mmol) of 4-acetoxy-2-(chloromethyl)-3,5,6-trimethylphenol [prepared according to L. I. Smith and R. B. Carlin, *J. Am. Chem. Soc.*, (1942), 64, 524–527] and 2.13 g (11 mmol) of methallyl-(4-nitrophenyl) ether (prepared according to German Published Patent Application No. 1,925,112) were suspended, under nitrogen, in 18.2 g of dichloromethane. 0.25 g (0.5 mmol) of scandium trifluoromethanesulfonate (Fluka) was then added, and the mixture was heated to reflux for 1.5 hour. 16 g of ice was then added to the reaction mixture, and the aqueous phase was separated off. The organic phase was washed with 20 ml of water and then with 4×20 ml of saturated sodium hydrogencarbonate solution, dried with sodium sulfate and evaporated on a rotary evaporator. The dried residue (3.53 g) had a content of 71.9 percent according to HPLC analysis. The yield was 63.6 percent (based on the chloromethyl compound). The crude product was dissolved in 20 g of boiling ethanol, and the solution was slowly cooled to room temperature and then maintained at 5° C. for a further 3 hours. The precipitated product was then filtered off using a glass suction filter, washed with about 2 ml of cold ethanol and dried. The content of the product recrystallized in this way was about 98 percent according to $^1$H NMR. For further purification and characterization, a sample was chromatographed with hexane/ethyl acetate (6:1) on aluminum oxide. The melting point of the product was 128° C. (from cyclohexane). Other data concerning the product was:

$^1$H NMR(CDCl$_3$):δ8.19/6.98(AA'XX',4H);4.11/4.01(AB,J=3Hz,2H);2.65 (m,3H);2.34(s,3H);2.14(m,1H);2.05(s,3H);2.02s,3H);1.98s,3H);1.90 (m,1h);1.43s,3H).

EXAMPLE 2

4-[(6-Acetoxy-2,5,7,8-tetromethylchroman-2-yl)methoxy]benzaldehyde $(I, R^1=R^3=R^5=R^6=Me, R^2=4-C_6H_4CHO, R^4=Ac)$ 38.32 g (150 mmol, 95 percent strength) of 4-acetoxy-2-(chloromethyl)-3,5,6-trimethylphenol and 25.11 g (142.5 mmol) of 4-(2-methyprop-2-enyloxy) benzaldehyde were suspended, under nitrogen, in 217.4 g of dichlormethane. 1.90 g (3.8 mmol) of scandium trifluoromethanesulfonate was then added, as a result of which a dark red suspension formed in a slightly exothermic reaction. This suspension was refluxed for a total of about 23 hours, 5 g of activated carbon being added after 5 hours. The reaction mixture was then filtered and washed successively with 100 ml of each of water, saturated sodium hydrogencarbonate solution and 10 percent strength sodium chloride solution The organic phase was dried over sodium sulfonate and evaporated on a rotary evaporator to leave 58.08 g of an oily crude product with a content of about 60 percent, which corresponds to a yield of 61 percent (based on the chloromethyl compound). For purification, the crude product was chromatographed with hexane/ethyl acetate (v:v=6.1) on aluminium oxide and, after the eluate had been evaporated, was suspended in ethanol, filtered and dried. The melting point of the product was 89° C. Other data concerning the product was:

$^1$H NMR(CDCl$_3$):δ9.87(s,1H);7.82(m,2H);7.03(m,2H);4.10d,J=10Hz, 1H);3.98(d,J=10Hz,1H);2.64(m,3H);2.34(s,3H);2.13(m,1H);2.07(s, 3H);2.02(s,3H);1.99(s,3H);1.89(m,1);1.44(s,3H).

IRv1785;1692 cm$^{-1.}$

MS[m/z]382(M$^{+,}$24%);340(100);219(15);205(61);203(15);191(13); 165(50);121(12);91(16);43(49).

What is claimed is:

1. A process for the preparation of chroman derivatives of the formula:

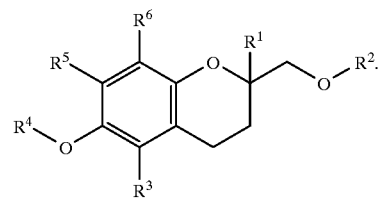

I in which:

$R^1$ is hydrogen or $C_{1-4}$-alkyl, $R^2$ is $C_{1-6}$-alkyl, $C_{3-6}$-cycloalkyl, optionally substituted aryl or optionally substituted aryl-$C_{1-6}$-alkyl, $R^3$, $R^5$ and $R^6$ independently of one another are hydrogen, halogen, $C_{1-4}$-alkyl or optionally substituted aryl, and $R^4$ is $C_{1-6}$-alkyl, $C_{3-6}$-cycloalkyl, (C-$_{1-6}$-alkoxy)methyl, optionally substituted aryl, optionally substituted aryl-$C_{1-6}$-alkyl, $C_{1-6}$-alkanoyl or optionally substituted aroyl, characterized in that a hydroquinone derivative of the formula:

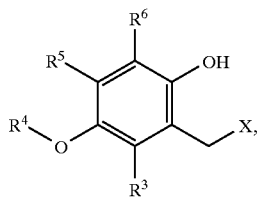

in which $R^3$ to $R^6$ are as defined above, and X is a leaving group, is reacted in the presence of a Lewis acid, with an alkene of the formula:

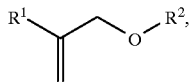

in which $R^1$ and $R^2$ are as defined above.

2. The process according to claim 1, wherein $R^1$ is methyl.

3. The process according to claim 2, wherein $R^2$ is optionally substituted aryl.

4. The process according to claim 3, wherein $R^2$ is p-nitrophenyl or p-formylphenyl.

5. The process according to claim 4, wherein $R^3$, $R^5$ and $R^6$ are methyl groups.

6. The process according to claim 5, wherein $R^4$ is acetyl.

7. The process according to claim 6, wherein X is chlorine.

8. The process according to claim 7, wherein the Lewis acid is a compound selected from the group consisting of boron trifluoride, aluminium chloride, titanium(IV) chloride, scandium trifluoromethanesulfonate, iron (III) chloride, zirconium(IV) chloride and tin(IV) chloride.

9. The process according to claim 8, wherein the reaction is carried out in a solvent selected from the group consisting of dichloromethane, chloroform, tetrahydrofuran and ethyl acetate.

10. The process according to claim 1, wherein $R^2$ is optionally substituted aryl.

11. The process according to claim 10, wherein $R^2$ is p-nitrophenyl or p-formylphenyl.

12. The process according to claim 1, wherein $R^3$, $R^5$ and $R^6$ are methyl groups.

13. The process according to claim 1, wherein $R^4$ is acetyl.

14. The process according to claim 1, wherein X is chlorine.

15. The process according to claim 1, wherein the Lewis acid is a compound selected from the group consisting of boron trifluoride, aluminium chloride, titanium(IV) chloride, scandium trifluoromethanesulfonate, iron (III) chloride, zirconium(IV) chloride and tin(IV) chloride.

16. The process according to claim 1, wherein the reaction is carried out in a solvent selected from the group consisting of dichloromethane, chloroform, tetrahydrofuran and ethyl acetate.

* * * * *